(12) United States Patent
Kaiya

(10) Patent No.: US 10,105,279 B2
(45) Date of Patent: Oct. 23, 2018

(54) MALE SEXUAL DYSFUNCTION SUFFERER-USE NEGATIVE PRESSURE ASSISTANCE DEVICE

(71) Applicant: Ichirou Kaiya, Yamagata (JP)

(72) Inventor: Ichirou Kaiya, Yamagata (JP)

(73) Assignee: Ichirou Kaiya, Tokyo (JP)

( * ) Notice: Subject to any disclaimer, the term of this patent is extended or adjusted under 35 U.S.C. 154(b) by 195 days.

(21) Appl. No.: 14/894,054

(22) PCT Filed: Jun. 4, 2014

(86) PCT No.: PCT/JP2014/064875
§ 371 (c)(1),
(2) Date: Nov. 25, 2015

(87) PCT Pub. No.: WO2014/196577
PCT Pub. Date: Dec. 11, 2014

(65) Prior Publication Data
US 2016/0095786 A1    Apr. 7, 2016

(30) Foreign Application Priority Data

Jun. 4, 2013   (JP) ................................. 2013-129980

(51) Int. Cl.
*A61H 9/00* (2006.01)
*A61F 5/41* (2006.01)
*A61H 19/00* (2006.01)

(52) U.S. Cl.
CPC ............. *A61H 9/0057* (2013.01); *A61F 5/41* (2013.01); *A61H 19/32* (2013.01); *A61F 2005/412* (2013.01)

(58) Field of Classification Search
CPC ..... A61F 2005/412; A61F 5/41; A61H 19/32; A61H 9/0057
See application file for complete search history.

(56) References Cited

U.S. PATENT DOCUMENTS

| | | | |
|---|---|---|---|
| 4,671,262 A | 6/1987 | West | |
| 7,083,570 B2 | 8/2006 | Bonthuys | |
| 8,382,656 B1 | 2/2013 | Brown | |
| 2001/0044569 A1 | 11/2001 | Naghar | |
| 2004/0171911 A1 | 9/2004 | Zurita | |

(Continued)

FOREIGN PATENT DOCUMENTS

| | | |
|---|---|---|
| CN | 2131508 Y | 5/1993 |
| CN | 1263452 A | 8/2000 |
| CN | 2714004 Y | 8/2005 |

(Continued)

OTHER PUBLICATIONS

Chinese Notification of the First Office Action corresponding to Application No. 201480031418.7; dated Aug. 2, 2016, with English translation.

(Continued)

*Primary Examiner* — Christine H Matthews
(74) *Attorney, Agent, or Firm* — Cantor Colburn LLP

(57) ABSTRACT

Provided is an assistance device comprising a hard sheath that simulates an erect penis and that has on the end thereof an air-bleed hole, and a soft skin that covers the entire hard sheath and that has an air-bleed hole at a position that is slightly offset from the air-bleed hole of the hard sheath, and the device has added thereto a valve function due to the two air-bleed holes.

2 Claims, 4 Drawing Sheets

(56) References Cited

U.S. PATENT DOCUMENTS

2010/0204542 A1    8/2010   Hodge

FOREIGN PATENT DOCUMENTS

| | | |
|---|---|---|
| CN | 201005834 Y | 1/2008 |
| DE | 4225160 A1 | 12/1992 |
| JP | H0237180 B2 | 8/1990 |
| JP | 05103805 A | 4/1993 |
| JP | 05103806 A | 4/1993 |
| JP | 05103807 A | 4/1993 |
| JP | 07080017 A | 3/1995 |
| JP | 3080245 U | 9/2001 |
| JP | 2002512080 A | 4/2002 |
| JP | 4381843 B2 | 12/2009 |
| JP | 2010515473 A | 5/2010 |
| WO | 2011146948 A2 | 11/2011 |

OTHER PUBLICATIONS

European Search Report corresponding to Application No. 14807678.9-1664 / 3005994 PCT/JP2014064875; dated Mar. 7, 2017.
Korean Office Action corresponding to Application No. 10-2015-7034378; dated Jan. 18, 2017, with English translation.
International Search Report corresponding to Application No. PCT/JP2014/064875; dated Jul. 8, 2014, with English translation.

MALE SEXUAL DYSFUNCTION SUFFERER-USE NEGATIVE PRESSURE ASSISTANCE DEVICE

This is the U.S. national stage of application No. PCT/JP2014/064875, filed on Jun. 4, 2014. Priority under 35 U.S.C. § 119(a) and 35 U.S.C. § 365(b) is claimed from Japanese Application No. 2013-129980, filed Jun. 4, 2013, the disclosure of which is also incorporated herein by reference.

TECHNICAL FIELD

The present invention relates to an assistance device that has been developed for a person with sexual dysfunction, and more particularly, to a male sexual dysfunction sufferer-use negative pressure assistance device that is prevented from falling out of a penis by the use of the negative pressure.

BACKGROUND ART

For a person suffering from sexual dysfunction, regardless of medical treatment, for example, similarly to glasses, hearing aids, an artificial arm, an artificial leg or the like, in achieving the intended purpose that supplements the physical dysfunction and physiological phenomena using some assistance devices, there is a significance of the sexual dysfunction sufferer-use assistance device.

Conventionally, as those similar to an assistance device that has been developed for a person with sexual dysfunction, various sack-like devices mounted to the penis of the user to disguise to a state of erection have been known. Also, a device in which the penis is in the state of erection using a negative pressure aspirator, a tightening ring is mounted on a base portion, and the negative pressure aspirator is detached to perform a sexual activity has also been suggested. Furthermore, there is a device in which the penis is tightened into a state of erection using a tubular rubber, and by covering an outer tube covering them, while maintaining the state of the erection, the sexual activity is continued by a negative pressure application.

Among the above-mentioned devices, as for a sack-like device, there is also a device that is affixed to the body with a belt. However, since there is not the sense of unity with the penis of the user, including these devices and the like, the sense of discomfort at the time of use cannot be denied, and there is a problem of easily falling out.

In addition, in a device that causes the state of erection by tightening the penile portion, any tightening device does not satisfy the state of erection. Therefore, even in a device that maintains the sexual activity by the negative pressure application by covering the outer tube for covering them, while maintaining the state of erection, there is a question in achievement of the integration with the penis.

As a measure to solve the above-described problems, inventions described in JP 5-103805 A (PTL 1), JP 5-103806 A (PTL 2) and JP 5-103807 A (PTL 3) have been suggested. For example, the invention described in JP 5-103806 A is configured to expose the glans of the user from the front end of the cylindrical main body by rewinding after winding the cylindrical main body to be fitted onto the penis of the user.

Furthermore, in the invention described in JP 5-103807 A, there is a device including a glans fixing chamber, an inner tube including a glans fixing ring with a diameter formed to be small in a neck portion of the glans fixing chamber and a penis fixing blade separated into a plurality of pieces from a front end, and an outer tube which is made of a windable flexible material and includes a glans portion that covers the glans fixing chamber of the inner tube and a penile portion that covers the penis fixing blade from the front end, and after housing the glans of the user in the glans fixing chamber by expanding the penis fixing blade of the inner tube, the penis fixing blade is closed to fix the inner tube to the penis by the glans fixing ring, and the wound outer tube is rewound from the front end of the inner tube, thereby sequentially mounting the device.

CITATION LIST

Patent Literature

{PTL 1} JP 5-103805 A
{PTL 2} JP 5-103806 A
{PTL 3} JP 5-103807 A
{PTL 4} JP 1610726 B1
{PTL 5} JP 4381843 B1
{PTL 6} JP 2010-515473 A (WO2008/083435)

SUMMARY OF INVENTION

Technical Problem

The above-described various background arts disclose a technique for setting the penis in the state of erection, but there is a limit to continuously maintain the erection state and it is nearly impossible. Thus, it is possible to mount the device without erection at all, and a device capable of achieving the object of the sexual activity should be assumed. Therefore, there is a need to inevitably adopt a hard sack-like device that simulates the erect penis. Furthermore, there is a need to devise a mechanism that eliminates the disadvantages of the sack-like device. Further, in terms of the shape, the material and the function, the device should be mounted to a user and a female partner without discomfort and can be accepted. Furthermore, a measure in which a man himself does not also involve the tightening activity so that he can aware of the normal sexual activity is desired.

Solution to Problem

To solve the above problem, in the present invention, there is provided a male sexual dysfunction sufferer-use negative pressure assistance device including: a hard sack with a shape that simulates an erect penis of a man into which a penis is inserted; and a soft skin made of a silicone rubber that covers the entire outside of the hard sack, by arranging an air vent hole at a front end of the hard sack, and by also arranging an air vent hole at a position that is slightly deviated from the air vent hole at the front end of the soft skin, the device added with a valve function in which while air in the hard sack is discharged to the outside through the air vent hole arranged at the front end of the soft skin from the air vent hole arranged at the front end of the hard sack, the air vent hole arranged at the front end of the hard sack is closed by the soft skin to prevent entry of outside air in a state in which the interior of the hard sack is in a negative pressure.

In addition, in the present invention, there is provided a male sexual dysfunction sufferer-use negative pressure assistance device including: a hard sack with a shape that simulates an erect penis of a man into which a penis is inserted; and a soft skin made of a silicone rubber that covers the entire outside of the hard sack, by arranging an air vent hole is placed at a front end of the hard sack, and by placing a plug that freely opens and closes the air vent hole placed at a position facing the air vent hole in the soft skin, the device added with a valve function in which air in the hard sack is discharged to the outside from the air vent hole arranged at the front end of the hard sack, and in a state in which the air vent hole is closed by the plug, a valve function in which the air vent hole is closed to prevent entry of outside air.

In the male sexual dysfunction sufferer-use negative pressure assistance device of the present invention, a hard sack that simulates the erect penis is used as a body. The hard sack is desirably formed of an outer shell portion formed of a hard material that simulates the erect penis, and a soft rubber-like material placed inside the outer shell portion. The soft rubber-like material is configured as a material that has feeling similar to the interior of a woman's vagina, and its base portion prevents the inflow of air, while facilitating the insertion of the penis. That is, the hard sack serving as the body has a two-layer structure, and an air vent hole is preferably arranged at its front end. In addition, a soft skin that covers the entire hard sack has feeling similar to the male penis. At the front end of the soft skin, the air vent hole is arranged at a position that is slightly deviated from the air vent hole of the hard sack, thereby achieving a valve function that discharges the air in the hard sack to the outside.

Even in the penis that is not in the state of erection, its mass or volume is not much different from the erect penis. The size of the hard sack is a size that satisfies its standard capacity. Therefore, even in the penis of a state like mollusks, the penis is inserted into the hard sack while the hard sack is pressed against the body, the penis comes into close contact with the hard sack at the same time of reaching near the front end air vent hole, and both of them maintain the state of the integration. That is, once the penis is inserted into the hard sack, when the inserted penis atrophies, since the negative pressure and the suction are accompanied, it increasingly comes into close contact with the body and integrated without falling out.

When mounting the assistance device according to the present invention, since there is no need for a belt or the like, and the penis is not tightened, a man himself is also aware of the normal sexual activity. As the soft skin that covers the entire hard sack, a silicone rubber is preferable, and since a female partner side rarely feels discomfort, it can be accepted as a penis of a male partner rather than as a foreign matter.

Although the present invention relates to a sexual dysfunction sufferer-use assistance device for negative pressure application devised for men suffering from erectile dysfunction mainly caused by an old age, further effects are also expected for young men who are in the impotence state due to diabetes, hypertension, stress, and the like.

Here, the features of the present invention will be described. That is, the present invention is to clarify the problem of facilitating the insertion of the penis that is not in the state of erection, among the several problems described above. The penis resembles a rubber cord. That is, it is rich in elasticity, it atrophies at the time of maximum 1.5 to 2 times in an acceptable place of a woven cloth, and the force to be restored is also maximum. A spongy tissue responsible for the erection of the penis is a sponge-like erectile tissue. During erection of the male penis, most of the penis spongy tissues are occupied by blood. When the penis is tried to be inserted into the hard sack that constitutes the assistance device of the present invention, it is inserted from the glans portion, while pressing the periphery of the base portion of the hard sack, the penis of a state like mollusks is inserted to be pushed. Therefore, the hard sack of about 15 cm is required especially in length, which requires allowable contents of exceeding the volume of the penis.

Therefore, when inserting about 15 cm to the air vent hole at the front end, the penis enters a longest state that can be stretched. The penis itself is not erect even in this state, rather contracted, and it is possible to pull the entire hard sack on which a force trying to restore acts against the body. Therefore, a phallus equipped with a hard sack of the present invention is integrally in close contact with the body as if there is a root.

Advantageous Effects of Invention

The present invention is a sexual dysfunction sufferer-use assistance device for negative pressure application devised for men suffering from erectile dysfunction mainly caused by an old age. Meanwhile, as an effect of the present invention, even the penis is in the state of impotence, there is provided an assistance device that makes it possible to perform the sexual activity. That is, there is provided an assistance device that also allows the sexual activity for young men in the impotence state caused by diabetes, hypertension, stress or the like. In particular, in a couple, in view of cases of divorce due to a trouble caused by a failure in sexual activity, the role of the present invention which prevents the cases in advance to allow attainment of smooth sexual activity is quite enormous.

In the present invention, a hard sack that simulates the erect penis is made up of an outer shell portion made of a hard material that simulates an erect penis, and a soft rubber-like material integrally placed on its inner side, the soft rubber-like material has feeling similar to the interior of the woman's vagina, and its base portion is configured to prevent inflow of air, while facilitating the insertion of the penis. That is, the hard sack serving as the body has a two-layer structure, and the air vent hole is arranged at its front end. Further, the hard sack is covered with a soft skin with feeling similar to the male penis. The air vent hole is arranged at the front end of the soft skin at a position that is slightly deviated from the air vent hole of the hard sack, thereby achieving a valve function that discharges the air in the hard sack to the outside. That is, at the time of attachment of an assistance device of the present invention, since there is no need for a belt or the like and the penis is not also tightened, a man himself is aware of a normal sexual activity.

In addition, even by closing the air vent hole placed at the front end of the hard sack though a plug after the penis insertion, the device can be mounted. At this time, the penis attempts to atrophy, and the interior of the hard sack becomes a negative pressure, thereby making it possible to improve the integrity with the penis.

The soft skin that covers the entire hard sack is preferably formed of a silicone rubber, and since a female partner rarely feels discomfort, it can be accepted as a penis of a male partner rather than as a foreign matter.

Any waste of their structures and mechanisms of the present invention are omitted, while maximizing the benefits for the negative pressure application, thereby minimizing the discomfort that is the greatest concern events in various assistance devices. The physical functions and physiological effects of the present invention are likely to be almost perfect matters without concern reasons.

Figure 1:
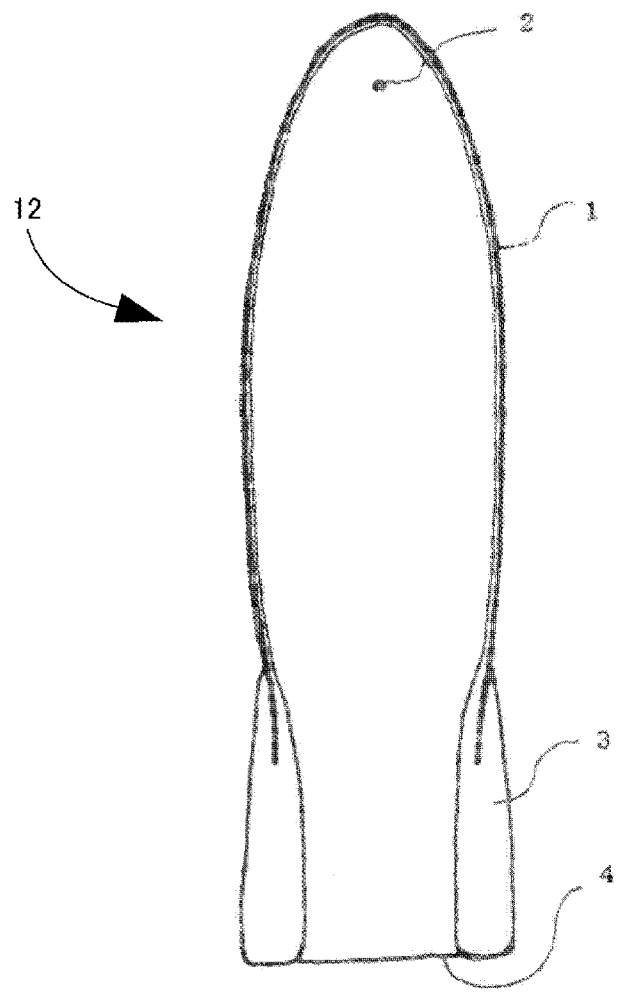
FIG. 1 is a vertical cross-sectional view taken along a lengthwise direction of a hard sack.

REFERENCE SIGNS LIST 1 outline portion of hard sack
2 air vent hole of hard sacks
3 silicone rubber portion of inner side and base portion of hard sack
4 inner diameter of base portion of silicone rubber
5 soft skin
6 air vent hole of soft skin

DESCRIPTION OF EMBODIMENTS

On using the assistance device according to the present invention, a user needs to explain a partner that the device is manufactured with safety without discomfort or incompatibility, and needs to obtain the consent.

At the time of use, first, hard sacks (1 and 3) are covered with a soft skin (5). A skin cream is desirably applied to the inner side of the hard sacks (1 and 3) and the penis to provide lubricity and air tightness. Further, a foreskin is covered over a glans portion by picking with a finger to be pushed to the hard sacks (1 and 3) and is inserted into the hard sack, while supporting the penis base portion. By hardly pressing the hard sack against the penis several times, while pressing the periphery of the base portion, that is, by pressing it against the penis while straining, the penis is inserted, while pressing and expanding a silicone rubber portion (4) of the hard sack base portion, and while discharging the air from the front end of air vent holes (2, 6). In a state in which the glans reaches the front ends of the hard sacks (1 and 3), that is, almost the air vent holes, the insertion is completed.

The hard sacks (1 and 3) and the penis are come into close contact with each other, and it is confirmed that both of them are integrated as if there is a root. Further, the sexual activity can be performed by applying a lubricating lotion to the soft skin (5) to be covered. Meanwhile, when detaching by picking the periphery of the air vent hole (6) of the soft skin (5) with a finger and by releasing the valve function, the negative pressure within the hard sack is decreased, and thus the device can be easily detached.

Next, referring to the drawings, a male sexual dysfunction sufferer-use negative pressure assistance device according to this embodiment will be described in detail. FIG. 1 is a vertical cross-sectional view taken along the lengthwise direction of the hard sack 12. The hard sack 12 has constant hardness and is configured to include an outer shell portion 1 formed to have hardness capable of maintaining a molded shape even at the time of use, and silicone rubber portions 3 and 4 that covers the inside of the outer shell portion 1 and covers the base portion of the outer shell portion 1. Among them, the outer shell portion 1 has a shape that simulates the penis of male and is formed to have a thickness capable of maintaining the constant shape using resin such as polypropylene, polyethylene and urethane. Further, the silicone rubber portions (3, 4) are desirably formed to have softness equivalent to an inner cavity using silicone resin in principle. However, it may be formed of other materials without being limited to silicone rubber. The length and inner and outer diameters of the hard sack 12 can be appropriately changed depending on race, age, body shapes or the like, and the average size over the race, the age or the like can be applied.

At a front end side of the hard sack 12, an air vent hole 2 penetrating through the outer shell portion 1 and the silicone rubber portions (3, 4) is formed. In particular, although there is no limit of the size, the air vent hole 2 may be a hole of about 2 mm. In addition, the air vent hole 2 does not necessarily need to be formed as an opening hole, but can be a cut formed, for example, in the outer shell portion 1 and the silicone rubber portions (3, 4). Even in the case of forming the air vent holes 2 as a cut, when discharging the air from the hard sack 12, the cut is opened to function as the an air vent hole 2.

Further, by placing the silicone rubber portions (3, 4) at the base portion of the outer shell portion 1, it is possible to enhance the adhesion in the root portion of the penis and to prevent air from entering the hard sack 12 from the root side of the penis. In addition, at the time of mounting, it is possible to give a soft impression to the wearer and to eliminate the discomfort caused by wearing.

Figure 2:
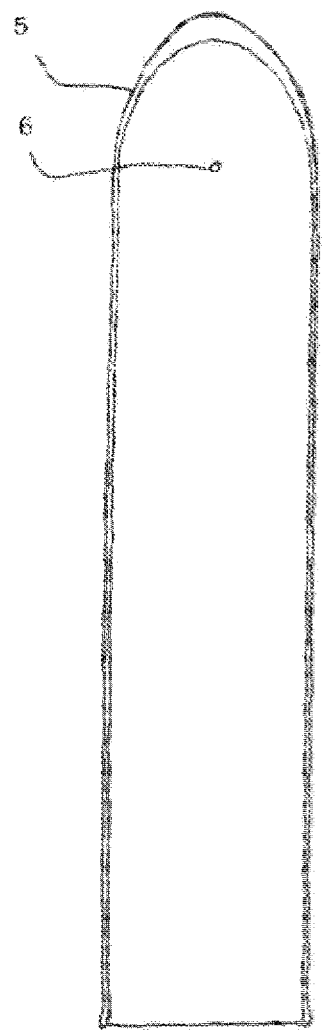
FIG. 2 is a vertical cross-sectional view taken along the lengthwise direction of a soft skin that covers the hard sack.

In addition, FIG. 2 illustrates a vertical cross-sectional view taken along the lengthwise direction of the soft skin 5 which covers the hard sack 12. The soft skin 5 primarily eliminates discomfort when it is inserted into the vagina and serves as an article for closing the air vent hole 2 formed in the hard sack 12 at the time of use. Furthermore, the soft skin 5 expresses the fine unevenness in the penis and can also serve to achieve a shape close to the penis of man. In this embodiment, the soft skin 5 is formed in a cylindrical shape with a closed front end, and the air vent hole 6 is formed on the front end side. The soft skin 5 can be formed using a resin having sufficient flexibility such as silicone and is formed to have a size capable of covering the outer surface of the hard sack 12. In this embodiment, although the portion formed in a cylindrical shape is particularly formed without unevenness, it may have a shape that corresponds to the outer shape of the hard sack 12, and unevenness or the like may be formed on the outer surface of the soft skin 5. Especially, at the time of use, in order to achieve the same feeling as the penis, minute unevenness, knurling or the like may be performed on its surface. Although the air vent hole 6 is also formed on the front end side of the soft skin 5, the air vent hole 6 needs to be formed at least a position that does not overlap with the air vent hole 2 formed in the hard sack 12. However, the air vent hole 6 formed in the soft skin 5 may also be formed as a cut.

Figure 3:
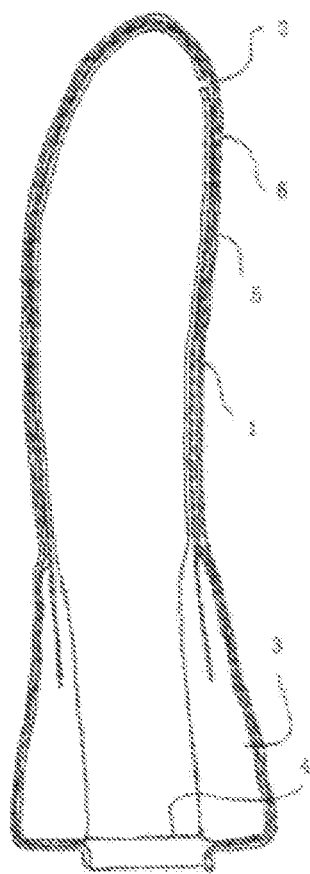
FIG. 3 is a vertical cross-sectional view taken along the lengthwise direction of a male sexual dysfunction sufferer-use negative pressure assistance device according to this embodiment.

FIG. 3 illustrates a state in which the hard sack 12 is covered with the soft skin 5, that is, FIG. 3 is a vertical cross-sectional view taken along the lengthwise direction of the male sexual dysfunction sufferer-use negative pressure assistance device according to the present embodiment. As illustrated in FIG. 3, the male sexual dysfunction sufferer-use negative pressure assistance device in this embodiment has a shape that is formed by the outer shell portion 1 of the hard sack 12, and the soft skin 5 is placed on its outer side. Also, silicone rubber portions 3 and 4 are placed on the inside of the outer shell portion 1. As a result, when a man wears it, the penis comes into contact with the silicone rubber portions 3 and 4, and the soft skin 5 comes into contact with in the vagina. Thus, since both are softy formed, it is possible to eliminate discomfort when wearing.

Figures 4A, 4B:
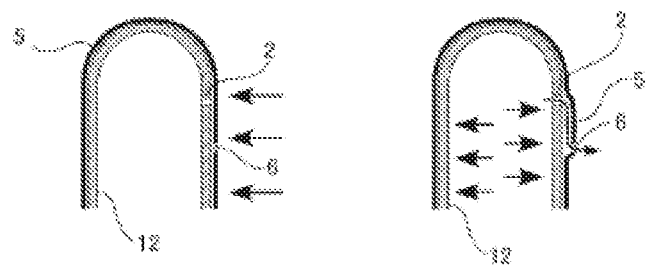
FIG. 4A is a vertical cross-sectional view schematically illustrating a negative pressure state in the hard sack.
FIG. 4B is a vertical cross-sectional view schematically illustrating a positive pressure state thereof.

Then, as illustrated in FIG. 3, the air vent hole 2 formed in the hard sack 12 and the air vent hole 6 formed in the soft skin 5 are formed at positions deviated from each other. As a result, as illustrated in FIG. 4A, in a state in which the internal space of the hard sack 12 is in the negative pressure, the air vent hole 2 of the hard sack 12 is closed by the soft skin 5 which makes it possible to prevent outer air from entering. Meanwhile, as illustrated in FIG. 4B, in a state in which the internal space of the hard sack 12 is in the positive pressure in the case of mounting or the like, the air discharged from the air vent hole 2 of the hard sack 12 moves between the hard sack 12 and the soft skin 5 while pressing and expanding the soft skin 5, and thus the air is discharged from the air vent hole 6 formed in the soft skin 5 to the outside.

Therefore, since the extra air in the hard sack 12 is discharged at the time of mounting and entry of air into the hard sack 12 is prevented at the time of use even when the inserted male penis attempts to atrophy, the negative pressure state is maintained within the hard sack 12, and thus, it is possible to reliably hold the assistance device in the penis.

Figure 5A:
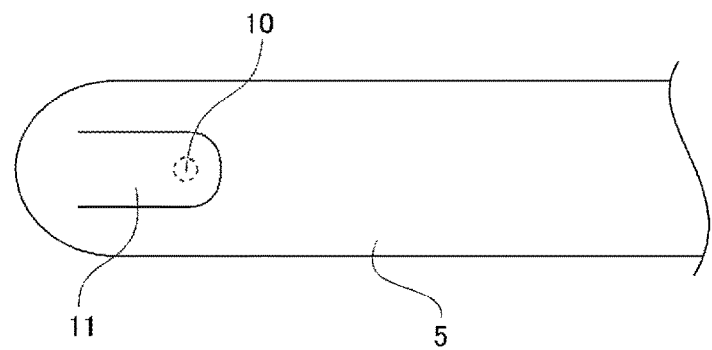
FIG. 5A is a plan view of a major part illustrating a valve mechanism of a male sexual dysfunction sufferer-use negative pressure assistance device according to another embodiment.
Figure 5B:
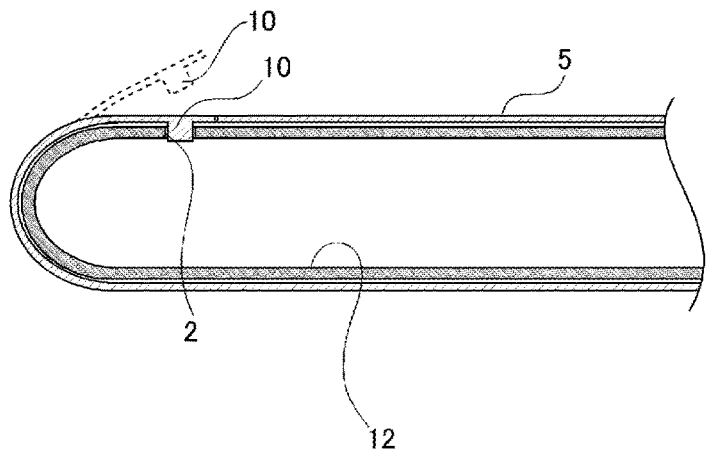
FIG. 5B is a vertical cross-sectional view thereof.

FIG. 5A is a plan view illustrating a valve mechanism of a male sexual dysfunction sufferer-use negative pressure assistance device according to another embodiment, and FIG. 5B is a vertical cross-sectional view thereof. The assistance device illustrated in FIGS. 5A and 5B illustrates an example in which an air vent hole 2 penetrating through the thickness direction is formed at the front end side of the hard sack 12, and a plug 10 configured to allow closing the air vent hole 2 is formed in the soft skin 5. In such an assistance device, at the time of mounting to the penis, a vent hole is in a released state, and after mounting, the vent hole is closed by the plug 10 to eliminate the risk of inflow of air to the hard sack 12 from the outside and to ensure the valve function. That is, even in the male sexual dysfunction sufferer-use negative pressure assistance device according to this aspect, by discharging the air in the hard sack 12 at the time of mounting and by keeping the inside of the hard sack 12 in the negative pressure state at the time of use, the integrity between the penis and the assistance device is enhanced, thereby eliminating the discomfort at the time of use.

In particular, in the embodiment illustrated in FIGS. 5A and 5B, the plug 10 configured to close the air vent hole formed in the hard sack 12 is formed integrally with the soft skin 5. More specifically, a flap portion 11 having cuts at three sides thereof is formed in the soft skin, and the plug 12 is formed on the flap portion 11. As a result, even if the plug 10 is detached for some reason during use since the plug 10 is held in the soft skin 5, it is possible to avoid the plug 10 from falling off. Moreover, the valve mechanism described in FIGS. 1 to 4 may be provided in combination with the plug 10 illustrated in FIGS. 5A and 5B.

Hereinbefore, although several specific examples have been illustrated with reference to the drawings in this embodiment, the present invention is not limited thereto and as long as they do not depart from the gist of the present invention, suitable changes can be applied.

INDUSTRIAL APPLICABILITY

The sexual dysfunction sufferer-use assistance device of the present invention is primarily devised for men who suffer from erectile dysfunction which is mostly caused by old age, it can also be used for young men who are in the impotence state due to diabetes, hypertension, stress, and the like. A penis wearing such an assistance device according to the invention is acceptable in a state of erectile dysfunction and can be used to impart a normal sexual life for a female partner, while a man himself is conscious of normal sexual activity in advance. In particular, as for couples, in view of cases of divorce due to a trouble caused by a failure in sexual activity, the role of the present invention which prevents these cases in advance to allow attainment of smooth sexual activity is quite enormous.

The invention claimed is:

1. A negative pressure assistance device for use on a male suffering sexual dysfunction comprising:
    a sack having a structure having an outer shape conforming to an erect penis shape of the male, and formed to have a constant hardness capable of maintaining a molded shape even at a time of use,
    a skin made of a silicone rubber which is softer than a material of the sack and covers an entirety of an outside of the sack,
    a first air vent hole being arranged at a front end of the sack to discharge air in the sack to the outside and to be closed by the skin to prevent entry of outside air in a state in which the interior of the sack is in a negative pressure, and
    a second air vent hole arranged at a front end of the skin slightly deviated from the first air vent hole to discharge the air vented from the first air vent hole to an outside of the skin.

2. The negative pressure assistance device according to claim 1, wherein the sack has a two-layer structure comprising an outer shell portion contacting with the skin and a soft material portion formed integrally up to a base portion of the outer shell portion.

* * * * *